United States Patent [19]
Brawn

[11] 3,977,395
[45] Aug. 31, 1976

[54] COMBINATION INHALATION AND EXHALATION RESPIRATORY THERAPY DEVICE

[76] Inventor: Peter Nelson Brawn, 36 Fairfield St., Pittsfield, Mass. 01201

[22] Filed: Feb. 20, 1975

[21] Appl. No.: 551,501

Related U.S. Application Data

[63] Continuation-in-part of Ser. No. 446,165, Feb. 27, 1974, abandoned.

[52] U.S. Cl................................. 128/2.08; 272/99
[51] Int. Cl.$^2$........................................... A61B 5/08
[58] Field of Search.................. 128/2.08, 2.07, 2 C; 272/57 F

[56] References Cited
UNITED STATES PATENTS

| | | | |
|---|---|---|---|
| 699,637 | 5/1902 | Aldrich............................ | 128/2.08 |
| 714,141 | 11/1902 | Cady................................. | 128/2.08 |
| 3,507,146 | 4/1970 | Webb................................ | 128/2.07 |
| 3,710,780 | 1/1973 | Milch ............................... | 272/57 F |
| 3,720,202 | 3/1973 | Cleary.............................. | 128/2.08 |
| 3,811,671 | 5/1974 | Turnbull ........................ | 128/2.08 |
| 3,848,585 | 11/1974 | Ostap............................... | 128/2.08 |

FOREIGN PATENTS OR APPLICATIONS

| | | | |
|---|---|---|---|
| 757,395 | 12/1933 | France............................. | 272/57 F |
| 415,914 | 9/1924 | Germany ......................... | 128/2.08 |
| 507,014 | 12/1954 | Italy ................................. | 128/2.08 |
| 18,558 | 4/1963 | Japan................................ | 128/2.08 |

*Primary Examiner*—Robert W. Michell
*Assistant Examiner*—Lee S. Cohen
*Attorney, Agent, or Firm*—Finnegan, Henderson, Farabow & Garrett

[57] ABSTRACT

A novel combination inhalation and exhalation respiratory therapy device is shown which allows measurement of the respiratory capacity of the user. Additionally, it is so constructed that the user or one supervising the user may control the rate of inspiration or exhalation while simultaneously measuring the total volume of air inhaled or exhaled. The respiratory therapy device, to be used with a liquid such as water, is comprised of two containers inter-connected by a conduit tube through openings in either the top wall portion or side wall portion of each respective container. Additionally, an opening is provided in the top wall portion of the first container to communicate atmospheric pressure to the surface of the liquid contained therein. A tube is fixedly mounted through the top wall portion of the second container having a user end adapted to be placed in the mouth of the patient. Various combinations of openings in the inter-connecting conduit, the upper wall portions of the containers or the fixed tube determine the respiratory effort required of the user to transfer a given amount of liquid from one container to the other. Additionally, the openings can be occluded selectively by occluding means such as larger diameter tube portions which are slideably mounted on the conduit means or fixed tube. In this manner the respiratory therapy device can be adjusted for the specific requirements of the user, with particular reference to respiratory rate and volume, without using unnecessarily large containers or complicated systems.

13 Claims, 13 Drawing Figures

COMBINATION INHALATION AND EXHALATION RESPIRATORY THERAPY DEVICE

BACKGROUND OF THE INVENTION

This application is a continuation-in-part application of Ser. No. 446,165, filed Feb. 27, 1974 and now abandoned.

The present invention relates to a simple respiratory therapy device which encourages both deeper respiratory inhalation and exhalation. This device finds particular application for patients with respiratory problems as for instance post-operative patients and those with atelectasis, pneumonia, chronic bronchitis and emphysema.

Often respiratory problems in patients are characterized by shallow breathing, failure to clear pulmonary secretion, and obstruction to proper oxygenation of their blood. In such situations there exists a need to encourage more efficient and deeper breathing.

There are presently several methods available for respiratory therapy. For instance, some devices are based upon a concept termed resistance expiration in which the resistance to air flow to the patient through the device is increased. However, this type of device requires a greater effort on the part of the patient for a given amount of air inhaled or exhaled and in general causes fatigue of the patient, thus discouraging use of such devices. This type of approach to respiratory therapy does not find general acceptance today.

Another device which is known as a rebreathing device uses a closed chamber such as a bag attached to the patient into which he inhales and exhales. Since the air supply is constant, the carbon-dioxide content increases while the oxygen content decreases. The patient therefor must increase his breathing in order to receive sufficient oxygen. This technique however merely causes the patient to breathe faster rather than deeper and is not a particularly safe method to use.

Intermittent positive pressure breathing has been utilized also. This method is applied to a patient by introducing forced blasts of air under pressure into the patient's mouth to provoke deep inhalation. Usually the equipment required is costly and complicated however and requires trained personnel to operate it. It may also result in detrimental side effects to the patient.

One additional prior art technique for encouraging deeper breathing utilizes two containers having liquid therein which are interconnected by a tube. Upon inhalation or exhalation efforts by the user liquid is transferred from one container to the second in a one to one ratio to the air inhaled or exhaled by the user. This particular device has the drawback of requiring rather large containers for the average adult patient who commonly has a respiratory volume requirement of 2-to-4 liters. Additionally such devices often offer undue restriction to liquid flow through the tubes causing fatigue to the user.

SUMMARY OF THE INVENTION

The present invention overcomes the problems of the prior art by providing a respiratory therapy device for use with a liquid which is simple and compact in size but which can be used with patients for whom different requirements are established as to respiratory volumes and respiratory rates of inhalation or exhalation. Considered in its broadest aspect, the combination inhalation and exhalation respiratory therepy device allows one to control the rate of inhalation or exhalation while simultaneously setting the desired respiratory volume for a single inhalation or exhalation. The device also is constructed to reduce the resistance to flow of liquid inherent in the tubes of the device.

In accordance with the purposes of the invention, as embodied and broadly described herein, the combination inhalation and exhalation respiratory therapy device of the invention comprises first and second closed containers interconnected by conduit means for conducting liquid between the containers, the first container having at least one opening in an upper wall portion thereof for communicating atmospheric pressure to the surface of the liquid contained in the first container, a tube having a plurality of openings on the side wall portion thereof which tube communicates through an upper wall portion of the second container and has a user end for application of a respiratory effort thereto. Usually occluding means can be mounted on the tube for selectively occluding the openings and thereby determining the ratio of respiratory volume of air withdrawn from or added to the container to liquid transferred from one container to the second container. Additionally, the openings can be selectively blocked so that a given constant respiratory effort applied to the user end of the tube results in a particular volume of liquid being displaced from one container to the other while a particular volume of air is being inhaled or exhaled.

Preferably, the containers are small of an order less than 1 liter in volume but still can be utilized with patients having a respiratory capacity of four or five liters.

It is also preferred that additional openings be provided in the conduit means which connects the first and second containers. Such openings permit additional mixing of air with the liquid being transferred from one container to the other and thereby reduce the resistance of the conduit means to the transfer of the liquid.

The invention consists in the novel elements, constructions, arrangements, combinations and improvements shown and described. The accompanying drawings, which are incorporated in and constitute a part of the specification, illustrate several embodiments of the invention and, together with the description, serve to explain the principles of the invention.

DESCRIPTION OF THE PREFERRED EMBODIMENTS

Reference will now be made in detail to the present preferred embodiments of the invention, examples of which are illustrated in the accompanying drawings.

Figure 1:
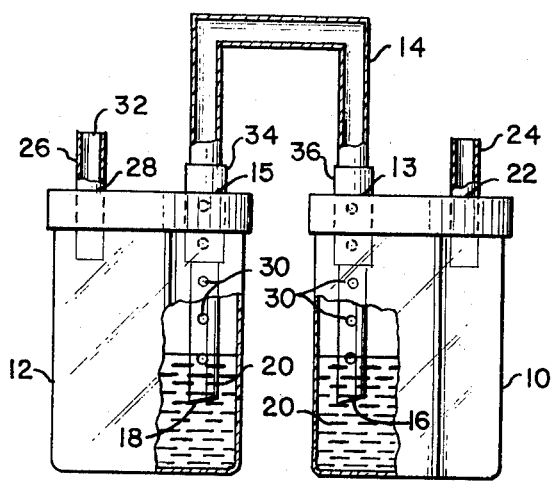
FIGS. 1 and 2 show one embodiment with portions shown in cross section in which the connecting conduit means has been adjusted to different positions relative to the containers.

Referring now to FIG. 1 there is shown a combination inhalation and exhalation respiratory therapy device according to this invention. A first closed container 10 made of a suitable material such as plastic or glass which is preferably translucent, is connected to a second closed container 12, made of a similar material by means of conduit means 14 through openings 13 and 15 in the upper wall portion of containers 10 and 12. Preferably the conduit means 14 is made of a flexible thin-walled tubing having a first end 16 projecting substantially to the bottom of container 10 and having a second end 18 projecting substantially to the bottom of container 12. Each of the ends 16 and 18 must project below the surface of the liquid 20 contained in the containers 10 and 12 during operation.

Conduit means 14 is adjustable up or down with respect to the containers as is explained below. But it will be understood, although not shown explicitly by FIG. 1, that flexible tubing of sufficient length would allow each end to remain on the bottom of each respective container even when conduit 14 is raised.

Preferably the first container 10 has at least one opening 22 through an upper wall portion which communicates atmospheric pressure to the surface of liquid 20 contained within the container 10. A tube 24 can be inserted in the opening 22 as shown in FIG. 1; however, such is necessary only if it is desirable to be able to interchange containers 10 and 12.

Preferably a tube 26 projects through an opening 28 in the upper wall portion of the second container 12 which has a user end 32 external of container 12 and into which a person may exhale or inhale. More specifically when in use the end 32 of tube 26 is placed in the mouth of the patient. The patient inhales or exhales through his mouth.

Still with reference to FIG. 1, it is preferred that the conduit means 14 have at least one opening in a side wall portion. As here embodied, a plurality of openings 30 increase the ratio of air to liquid transferred between containers 10 and 12 upon exhalation or inhalation efforts applied to the user end 32 of tube 26. The openings 30 as shown in FIG. 1 are in portions of the conduit 14 within the interior of the respective containers 10 and 12 and act to decrease the resistance effect of the conduit 14 to the transfer of liquid and air between the containers. Thus by mixing air with the liquid a lubricating effect is achieved reducing the frictional resistance of the interior tube walls to flow. Turbulence in the conduit must be avoided to gain this advantageous result, but this is not normally a problem in this type of device unless an excessive number of large openings were used.

It is preferred that occluding means as here embodied by fixed cylindrical elements 34 and 36 be fixedly mounted through openings 13 and 15 on containers 12 and 10 respectively. The interior diameters of these cylindrical elements 34 and 36 are approximately the same as the outer diameter of conduit means 14. The cylindrical tube portions 34 and 36 therefore surround a part of the conduit means 14 and can be moved relative to the conduit means to selectively occlude openings 30. Since the conduit 14 is preferably flexible, one portion of the conduit can be adjusted independent of the portion in the other container.

Figure 2:
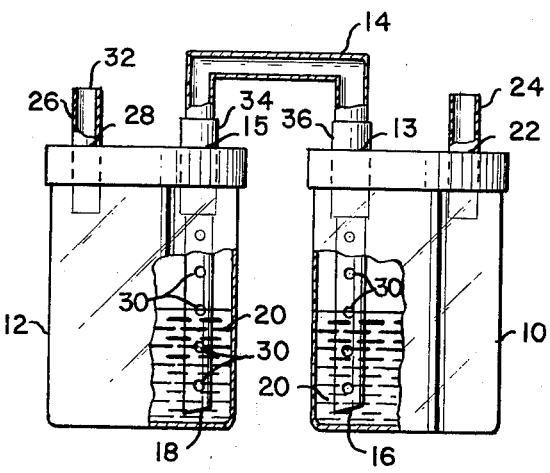

Referring now to FIG. 2, the same embodiment as shown in FIG. 1 is depicted but with the conduit means 14 adjusted to a position in which no openings are occluded by the cylindrical tube portions 34 and 36. In operation, the respiratory therapy device of FIGS. 1 and 2 can be used by a patient for either inhalation or exhalation therapy. The patient or user by placing the user end 32 of tube 26 in his mouth exerts a respiratory effort, either by inhalation or exhalation to breathe deeply thereby causing part of the liquid to move from the first container to the second container or vice versa due to the pressure differential created between the two containers.

At the beginning of the operation, the total amount of liquid in the two containers and conduit means 14 should be less than half of the total volume of the two containers combined. If more liquid is used, the patient or user will likely inhale some liquid or upon an exhalation effort blow liquid out of the first container 10.

If the openings 30 are not occluded by the cylindrical tube portions 34 and 36 and are opened to the air rather than the liquid 20, the result will be the mixing of air and liquid in the conduit means 14. The flow resistance in the conduit means 14 is effectively reduced. Thus the user upon an inhalation or exhalation effort will be able to move a smaller quantity of liquid and thereby a larger volume of air will be brought into or out of his lungs.

Figure 3:
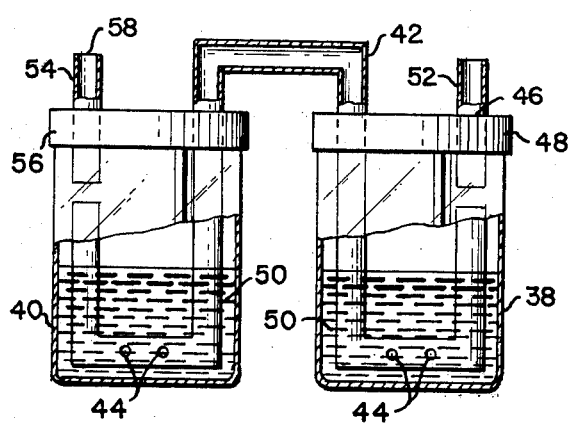
FIG. 3 is another embodiment shown schematically with portions in cross section.

Referring now to FIG. 3, a variation on the respiratory therapy device discussed above is shown having a first closed container 38 and a second closed container 40 connected by a conduit means 42 which is here embodied as a flexible tubing made out of a resilient material such as plastic. The device of FIG. 3 is a combination inhalation and exhalation respiratory therapy device to be used with a liquid. The conduit means 42 which connects the first and second containers 38 and 40 conducts liquid between the two containers and has openings 44 in several wall portions thereof. Preferably these wall portions of conduit 42 in which the openings are located are within the first and second containers 38 and 40.

It is also to be preferred that the first container 38 have at least one opening in the upper wall portion 48 thereof for communicating atmospheric pressure to the surface of the liquid 50.

A tube 52 can be fitted into the opening 46 as shown in FIG. 3. Such a tube is optional but if used allows the flexibility for the patient of being able to use either container 38 or 40 as the primary container into which to breathe.

Preferably tube means 54 passes through an opening in a wall portion 56 of the second container 40 and has a user end 58 external of the second container into which a person, through his mouth, may exhale or inhale.

One particular advantage of this variation is the placement of the openings 44 of conduit means 42 to be close to or at the bottom of the respective containers 38 and 40. Thus regardless of the level of liquid 50 in a given container, until one container is completely exhausted, liquid can be transferred through respiratory effort applied to the user end 58 of tube 54.

Figure 4:
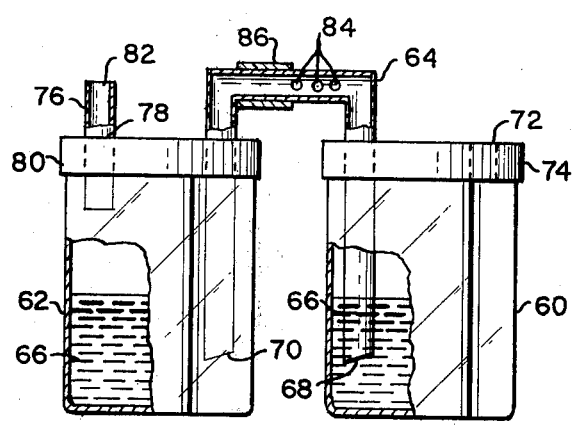
FIG. 4 is yet another embodiment shown schematically with portions in cross section.

Referring to FIG. 4, another embodiment of the combination inhalation and exhalation respiratory therapy device is shown. A first container 60 is connected to a second container 62 through conduit means 64 having ends 68 and 70 immersed in liquid 66. The first and second closed containers 60 and 62 hold liquid 66. An opening 72 is provided in top wall portion 74 of container 60.

It is also preferred that tube means 76 project through an opening 78 in the upper wall portion 80 of the second container 62 which has a user end 82 external of the container 62. A person or patient placing the user end 82 of tube means 76 to his mouth exhales or inhales into the tube 76 to operate the respiratory therapy device of FIG. 4.

As here embodied the conduit means 64 has openings 84 in a side wall portion of the conduit means itself. The openings 84 affect the ratio of air to liquid transferred between the containers 60 and 62 upon inhalation or exhalation effort applied to the user end 82 of the tube means 76. The more openings 84 not occluded, the greater the mixing effect thereby decreasing the resistance of the conduit means 64 to the flow and transfer of liquid and air from one container to the other.

As embodied in FIG. 4, the respiratory therapy device has occluding means here represented as a cylindrical tube portion 86. The tube portion 86 has an interior diameter of approximately the same size as the exterior diameter of conduit means 64. The occluding cylindrical tube portion 86 slides on the conduit means 64 thereby selectively occluding openings 84.

In operation, the respiratory therapy device of FIG. 4, allows air to be mixed through openings 84 with liquid being transferred between containers 60 and 62 through conduit means 64. Depending upon the effort applied by the user to the user end 82 of tube 76, more or less liquid 66 will be transferred from one container to the second container.

The openings 84 in conduit means 64 if not occluded by cylindrical tube portion 86 increase the ratio of air to liquid transferred between the containers upon a given inhalation effort while decreasing resistance effects of the conduit means 64 to the transfer of the liquid and air. The decreased resistance effect is primarily due to the introduction of air into the conduit means 64.

In the embodiments shown thus far in FIGS. 1, 2, 3 and 4, it will be clear that the placement of openings in various portions of the conduit means connecting the containers has a varying effect upon the ratio of the volume of air to liquid transferred and also an effect upon the resistance to flow through the conduit means. Each of the embodiments described thus far can be used to measure the capacity or volume of a single inhalation or exhalation effort by the user when calibrated to account for air which is mixed with the liquid during transfer. For instance, upon inhalation by the user, the liquid in the second container in each of the embodiments will rise to a new level. The new level would be indicative of the volume of the air drawn into the lungs of the user. Because of the openings in the conduit means there is not a one-to-one ratio of liquid transferred to volume of air inhaled. Nonetheless for any particular adjustment of each of the embodiments shown, the volume of air withdrawn through inhalation can easily be calibrated such that when a patient utilizes the device, he can quite easily translate a given level change in the containers to a certain volume of air inhaled.

Figure 5:
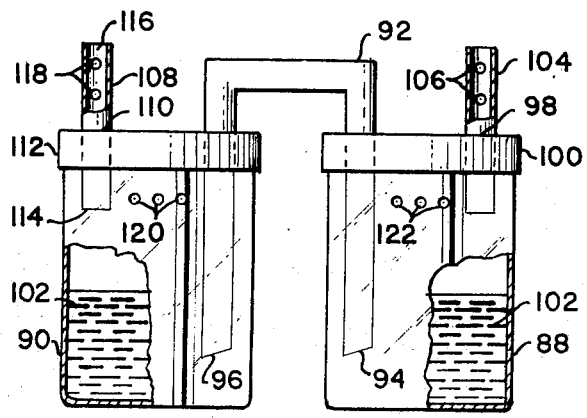
FIG. 5 is another embodiment shown schematically with portions in cross section and having openings in the upper wall portions of each container.
Figure 6:
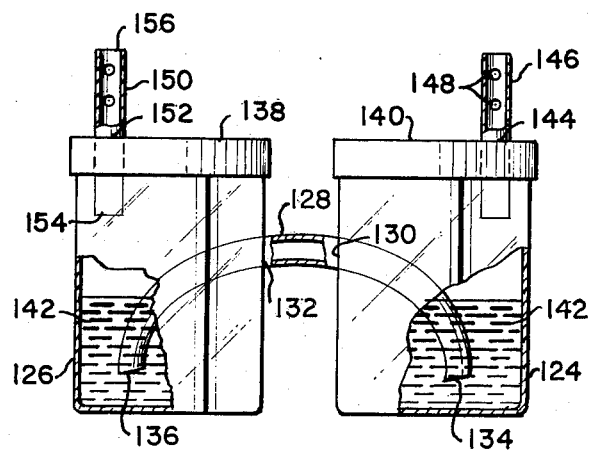
FIG. 6 is yet another embodiment shown schematically with portions in cross section and with the interconnecting conduit means projecting through side wall portions of each of the containers.
Figure 7:
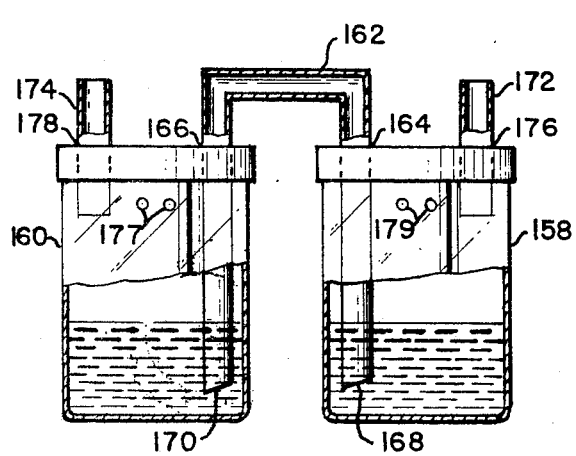
FIG. 7 shows another embodiment schematically which is a slight variation from that shown in FIG. 5.

Referring now to FIGS. 5, 6 and 7, additional embodiments of the present invention are shown in which the patient applies a constant respiratory effort to a tube so that the inhalation or exhalation rate is maintained constant and a given volume of liquid is thereby displaced from one container to the other. As long as the difference between levels is maintained constant indicative of the volume of liquid displaced, the rate of withdrawal of air from the container also is constant. By timing the period during which the fluid level difference between containers is maintained constant, an accurate measurement of the total volume of inhalation or exhalation is obtained. In another therapy application all the liquid can be moved from one container to the other or vice versa.

Referring now specifically to FIG. 5, a combination inhalation and exhalation respiratory therapy device has a first closed container 88 connected to a second closed container 90 through conduit means 92. Preferably the conduit means 92 conducts liquid between the containers 88 and 90 and has a first end 94 which projects into container 88 to a position adjacent the bottom of that container. A second end 96 of conduit means 92 projects into the second container 90 to a position adjacent the bottom of that container.

Preferably there is an opening 98 through the upper wall portion 100 of the first container 88 which provides means for communicating atmospheric pressure to the surface of the liquid 102. The means for communicating atmospheric pressure to the surface of the liquid 102 as embodied in FIG. 5 can further include a tube 104. Tube 104 projects through the opening 98 and is fixedly attached to the upper wall portion 100 of container 88. Further it is preferred that tube 104 have openings 106 in the upper wall portion of the tube.

Preferably there is also provided tube means 108 which projects through an opening 110 in the upper wall portion 112 of second container 90. The end 114 of tube means 108 is located well above the surface of the liquid 102 and can if desired be flush with the top interior wall. The tube means 108 is fixedly attached to the upper wall portion 112 having an exterior diameter approximating that of the opening 110.

It is preferred that tube means 108 have a user end 116 outside container 90 into which a person may exhale and inhale by placing the end 116 into his mouth.

It is further preferred that tube means 108 have at least one opening in a side wall portion thereof for increasing the ratio of the volume of air withdrawn from or blown into the second container 90 to the liquid transferred between the containers 88 and 90 upon inhalation or exhalation effort respectively applied to the user end 116 of the tube 108.

A further modification shown in FIG. 5 has openings 120 and 122 found in upper wall portions of containers 90 and 88 respectively. These openings function similarly to the openings 118 in tube 108 and openings 106 in tube 104. Upon inhalation or exhalation effort respectively applied to the user end 116 of tube 108, air is drawn in or pushed out of the openings 120 in the upper wall of container 90, thereby increasing the ratio of the volume of air withdrawn or blown into the second container 90 to the volume of liquid transferred between the containers. The openings 120 and 122 can be selectively occluded by plugs or corks not shown, which could effectively close off individual openings. In this manner the effect of the openings upon inhalation or exhalation effort by the user could be modified by occluding one or more of the openings.

Referring now to the combination inhalation and exhalation respiratory therapy device shown in FIG. 6, a further modification in design is shown. Preferably a first closed container 124 is connected to a second closed container 126 through conduit means 128. The conduit means 128 which conducts liquid between the containers projects through openings 130 and 132 in the upper side wall of containers 124 and 126 respectively. The conduit means 128 preferably made of a flexible resilient material such as plastic has a first end 134 which projects to a position adjacent to the bottom of the first container 124 and has a second end which projects to a position adjacent to the bottom of the second container 126.

Preferably means are provided for communicating atmospheric pressure to the surface of the liquid 142 contained in the first container 124. As here embodied, that means is in the form of an opening 144 in the upper wall portion 136 through which a tube 146 projects. The tube 146 being of substantially the same exterior diameter as that of the opening 144 is fixedly attached to the upper wall portion 136 of container 124. A plurality of openings 148 are formed in the side wall of tube 146.

Further, it is preferred that tube means, here embodied as tube 150, projects through an openings 152 in the upper wall portion 138 into the second container 126. The lower end 152 of tube 150 must be above the surface of the liquid 142 contained in the container 126. The user end 156 of tube 150 is outside of container 126 and is adapted for insertion into the mouth of a user.

It will be understood that the respiratory therapy device shown in FIG. 6 operates in substantially an identical manner to that shown in FIG. 5. The major structure modification is in the connection made by the conduit means 128 through openings 130, 132 in the side walls of the containers 124 and 126 respectively. This modification in structure has no essential effect upon the operation of the device.

FIG. 7 shows but a slight variation in the embodiment previously described in connection with FIG. 5. For the sake of simplicity the various elements of the combination inhalation and exhalation respiratory therapy device of FIG. 7 will not be described in detail. A first container 158 is connected to a second container 160 through conduit means 162. The conduit means 162 which passes through openings 164 and 166 in upper wall portions of the first and second containers 158 and 160 respectively has ends 168 and 170 which project substantially to the bottom of the respective containers.

Tubes 172 and 174 project through openings 176 and 178 respectively into the containers 158 and 160. Either tube 172 or 174 may be used by the patient by inserting the external end into his mouth and inhaling or exhaling into the tube.

No openings are provided in either of the tubes 172 or 174. However, there are provided a plurality of openings 177 in the upper side wall of container 160 and a plurality of openings 179 in the upper side wall of container 158. These openings act to increase the ratio between the volume of air withdrawn from or blown into the second container 160 to the volume of liquid transferred between the containers upon inhalation or exhalation efforts applied to the user end of tube mean 174. Of course, the operation is the same but reversed if the user instead breathes into tube 172.

Having now explained certain modifications in the combination inhalation and exhalation respiratory therapy device, it is important to understand the operation of this device more completely. Thus referring to FIGS. 8, 9, 10 and 11, it is possible to explain in detail the preferred operation of the respiratory therapy device to measure the rate of inspiratory or expiratory effort of the user and to measure the volume of air inhaled or exhaled by the user. Referring now in detail to FIGS. 8, 9, 10 and 11 and the combination inhalation and exhalation respiratory therapy device shown, there is a first closed container 180 connected to a second closed container 182 through a thin walled conduit means 184. The container 180 is closed by an upper wall portion 186 and container 182 is closed by an upper wall portion 188.

preferably conduit means 184 which conducts liquid between the containers 180 and 182, projects through openings 190 and 192 in the upper wall portions 186 and 188 respectively. The conduit means 184 has a first end 194 which projects into container 180 to a position adjacent the bottom of that container. Conduit means 184 further has a second end 196 which projects into the second container 182 to a position adjacent the bottom of that container.

Preferably means are provided for communicating atmospheric pressure to the surface of the liquid 198 in the first container 180 here embodied as an opening 200 in the upper wall portion 186. This communicating means can further include a tube 202 having an external diameter substantially the same as the diameter of the opening 200 and fixedly attached to the upper wall portion 186. Tube 202 is further provided with openings 204 in the side wall thereof.

Preferably tube means 206 similar to 204 projects through an opening 208 in the upper wall portion 188 of the second container 182. Tube 206 further has openings 210 in a side wall portion thereof. The openings 210 when not blocked increase the ratio of the volume of air withdrawn from or blown into container 182 to the volume of liquid 198 transferred between containers upon inhalation or exhalation effort applied to the tube means 206. It is further preferred that occluding means here embodied as a cylindrical tube portion 212 be mounted on the tube means 206. The cylindrical portion of tube 212 has an interior diameter slightly larger than the exterior diameter of tube 206, thereby sliding over 206 in a frictional fit. The cylindrical tube portion 212 selectively occludes holes 210 so that for a constant inhalation or exhalation rate applied to the upper end of the tube 206 a constant volume of liquid 198 will be displaced from one of the containers to the other. As long as the inhalation or exhalation rate is applied constantly to tube 206, a constant difference in levels of liquid in the containers is maintained. As here used the inhalation or exhalation rate is meant to mean the volume of air inhaled or exhaled by the user per unit of time.

By moving the occluding cylindrical tube portion 212 upward on tube 206 to occlude selectively holes 210, the amount of air inhaled or exhaled by the user through tube 206 can be increased or decreased for a given respiratory effort.

Figure 8:
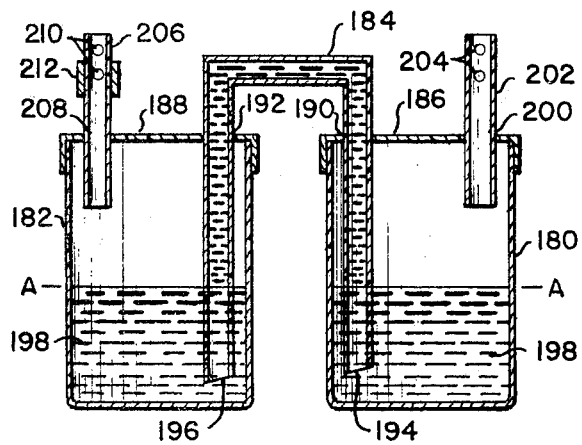
FIGS. 8, 9, 10 and 11 show the same embodiment under different conditions of occluding adjustments and applied respiratory effort.

In FIG. 8, the device is at its initial stage of equilibrium with liquid 198 at the level indicated by the letter A in each of the containers 180 and 182 and conduit 184 filled with liquid. The operation of this embodiment is discussed for inhalation although its application for exhalation will be clear too.

Figure 9:
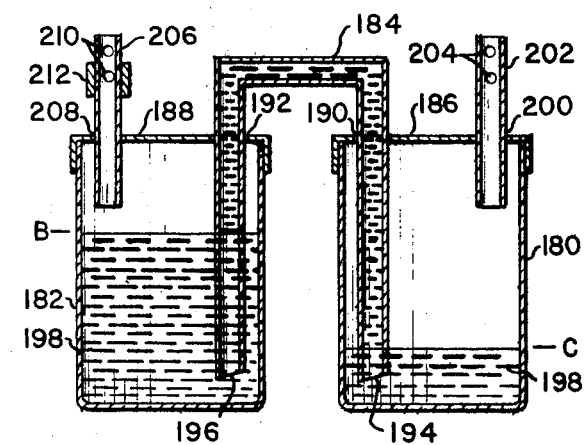

With selected holes 210 occluded by the cylindrical tube portion 212 as shown in both FIGS. 8 and 9, the liquid level in container 196 is raised when a given constant inhalation effort is applied to tube 206 thereby reducing the pressure on the surface of the liquid in container 182. As shown in FIG. 9, this level is indicated by the letter B. Simultaneously, the level of liquid in container 180 drops to a new level C. As long as the user maintains a constant rate of inhalation, i.e. volume of air withdrawn per unit of time, the difference in level will remain the same. Furthermore, if the user continues at the same rate for a given period of time, such as 5 seconds, one can calculate the total volume of air inhaled by the user. This calculation is simply the product of the period (5 seconds) times the rate of withdrawal of air, volume per unit of time.

Figure 10:
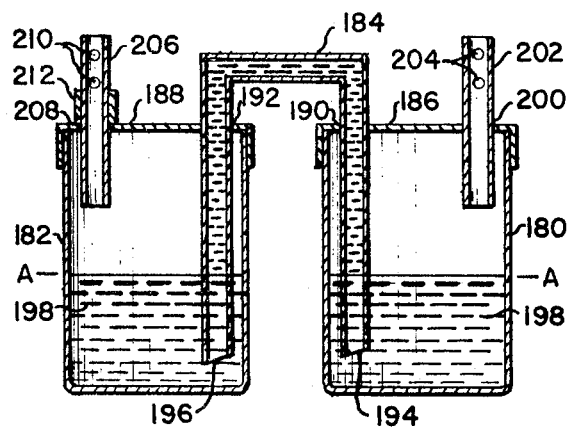
Figure 11:
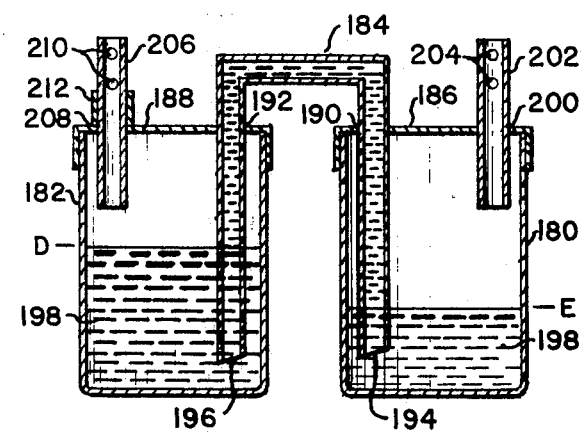

FIGS. 10 and 11 show the same embodiment for a second and different condition. In FIGS. 10 and 11, the occluding cylindrical tube portion 212 is moved downward to open to the atmosphere additional openings 210 in tube 206. In this case when the user applies an inhalation effort to the end of tube 206, there will occur a smaller change in the level of liquid 198 in container 182 for the same rate of withdrawal of air. This is reflected in FIG. 11 where for the same respiratory effort on the part of the user, the level of liquid 198 in container 182 is raised only to level D while the level in container 180 drops only to level E. This is due to the greater mixing of air through openings 210 with the air withdrawn from container 182 by the inhalation effort of the user.

For most therapy a low rate of inspiration is better for the patient. By use of the device of FIGS. 8, 9, 10 and 11 the user can be supervised in a manner to breath deeply (large volumes of air) but at a low rate of inspiration. In other devices which only measure the total volume inhaled or exhaled, the patient can increase the rate of inhaling or exhaling without the device detecting the difference.

when certain parameters and dimensions of the combination inhalation and exhalation respiratory therapy device of FIGS. 8 through 11 are known, a table can be prepared as a ready reference to show the amount of air being transferred into or out of the device by the user over various periods of time. One device has been constructed in which the first and second containers 180 and 182 were made of a plastic material and had a capacity of approximately one half liter. A flexible plastic tubing having an internal diameter of one half inch was used for all tubes (206 and 202) and for the conduit means 184. With two openings 210 of one-sixteenth inch diameter in the tube 206, a chart was prepared calibrated with the level of liquid in container 182 to give a direct reading of the volume of air inhaled by the user for various time periods. The volumetric amounts are given in cubic centimeters. The chart used with the above model is shown applied to the side of container 182 in FIG. 12.

Figure 12:
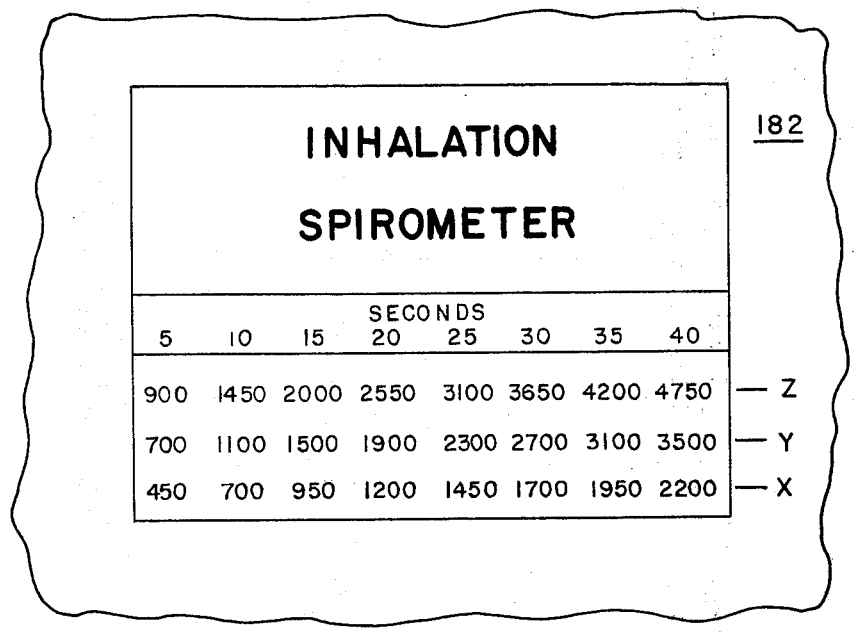
FIG. 12 shows a typical chart applied to the side wall of a container for establishing rates and volumes of respiration.

In FIG. 12, the table is affixed to the side of container 182 so that the marks X, Y, and Z, give the level to which the liquid must be raised within container 182 for the corresponding row of volumes of air withdrawn to apply. For instance, if the user raises the liquid to level X from a previously calibrated O level and holds the liquid at the level X for 15 seconds, 950 cc of air will be inhaled by the user. If the level of liquid is raised to level Z and held for 15 seconds by the user, then 2,000 cc of air will have been removed and inhaled by the user.

Figure 13:
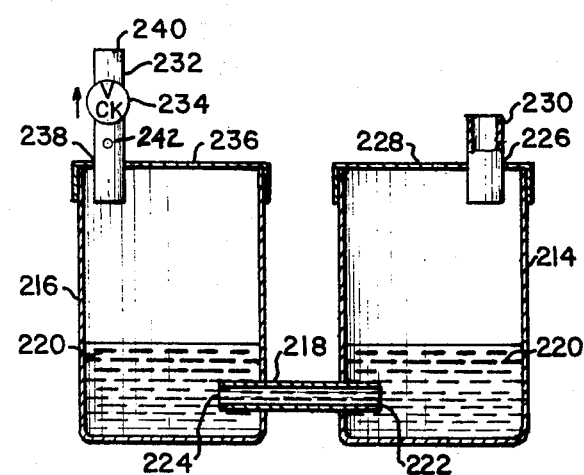
FIG. 13 shows schematically another embodiment utilizing a one-way valve for inhalation therapy only.

Referring now to FIG. 13, another embodiment is schematically shown for use as an inhalation therapy device only. Normally, inspiration or inhalation is the best therapy for a patient. Althrough may devices in the prior art utilize exhalation as the mode for therapy, it has been found that inhalation provides the best therapy and inhalation is generally the therapy to be preferred.

In FIG. 13, there is shown an inhalation respiratory therapy device having a first closed container 214 connected to a second closed container 216 through liquid carrying conduit means 218. Each container and the conduit means 218 hold a liquid 220 whose total volume is less than the total volume of the two containers combined.

It is preferred that the conduit means 218 project through respective side wall portions of the first and second containers 214 and 216 with a first end 222 located at substantially the bottom of the first container 214 and a second end 224 located at substantially the bottom of the second container 216. Preferably, the conduit means 218 is a thin walled tube of a resilient flexible material such that the ends 222 and 224 can easily be arranged at or near the bottoms of each of the respective containers.

Preferably the first container 214 has at least one opening 226 in an upper wall portion 228 for communicating atmospheric pressure to the interior of the first container 214. a thin walled tube 230 may also be mounted within the hole 226 in the upper wall portion 228 if so desired.

It is further preferred that tube means 232 including a one-way valve 234 which permits only withdrawal of air from container 216 be mounted on the upper wall portion 236 of container 216. Specifically, the tube 232 projects through openings 238 in the upper wall portion 236 and is fixedly attached thereto, the exterior diameter of tube 232 being substantially the same as the diameter of opening 238.

The one-way valve 234 is shown schematically in FIG. 13, but it will be understood by those skilled in the art that such a one-way valve can be easily incorporated into a flexible thin walled tube such as tube 232. a valve 234 could for instance be so constructed to have a flap of flexible material across the interior section thereof such that air flow is only permitted in one direction. Such a valve is common in the art.

Tube 232 has a user end 240 outside the second container 216 such that a person can apply inhalation effort thereto. When inhalation effort is applied to the user end 240 the one way valve 234 permits withdrawal of air from container 216.

Tube means 232 preferably has at least one opening 242 in a side wall portion thereof for increasing the volume of air withdrawn from the tube 232 as related to the volume of liquid 220 which is transferred from the first container 214 to the second container 216 for a given inhalation effort of the user. It will be appreciated that when inhalation effort is applied to the user end 240 of tube 232, reduction in pressure on the surface of liquid 220 in container 216, while substantially atmospheric pressure is applied to the surface of liquid 220 in container 214, will cause the liquid in the second container 216 to rise while the liquid in container 214 will be lowered.

It is possible with the inhalation respiratory therapy device of FIG. 13 to apply a table similar to that shown in FIG. 12 to the outside surface of the container 216. This table, properly calibrated for the particular container sizes and tube sizes, is used to measure the amount of air withdrawn by the patient over any given period of time covered by the chart. Thus this particular device which discourages exhalation efforts by the patient, provides inhalation therapy by which the user or one supervising the use may set up a regimen of therapy to include certain breathing exercises which require specific rates of inhalation and specific volumes to be withdrawn by the patient.

It is further to be understood that the combination inhalation and exhalation respiratory therapy device shown in the various figures are used to change from time to time the particular schedule or regimen to be followed by the patient in his respiratory therapy. Thus as the patient improves rates of inhalation or exhalation can be increased and volumes of air inhaled or exhaled can also be increased.

What is claimed is:

1. A combination inhalation and exhalation respiratory therapy device for use with liquid comprising:
   first and second closed containers for holding liquid;
   means connecting said first and second containers for conducting liquid between said containers, said means having first and second open ends projecting into said first and second containers respectively to substantially the bottoms thereof;
   said first container having at least one opening in an upper wall portion thereof for communicating atmospheric pressure to the surface of the liquid adapted to be contained therein;
   tube means projecting through a wall portion of said second container having a user end external of said second container into which a person may exhale or inhale through his mouth for moving air into and out of said second container; and
   said means for conducting liquid having at least one opening in a side wall portion thereof open to the atmosphere for increasing the ratio of air to liquid transferred between said containers upon exhalation or inhalation effort applied to said user end of said tube means and for decreasing resistance effects of said conducting means to transfer of liquid.

2. The combination inhalation and exhalation respiratory therapy device of claim 1 where said means for conducting liquid comprises a flexible thin-wall tube.

3. The combination inhalation and exhalation respiratory therapy device of claim 2 wherein said means for conducting liquid has a plurality of openings in a side wall portion thereof and further including occluding means adjustably mounted on said conducting means for selectively blocking said openings.

4. The combination inhalation and exhalation respiratory therapy device of claim 3 wherein said occluding means includes a cylindrical tube portion which surrounds a part of said conducting means and can be moved relative to said conducting means to selectively occlude said openings.

5. The combination inhalation and exhalation respiratory therapy device of claim 3 wherein said openings are in a portion of said conducting means interior of at least one of said containers.

6. The combination inhalation and exhalation respiratory therapy device of claim 5 wherein said occluding means includes first and second cylindrical tube portions surrounding respective parts of said conducting means and fixedly attached to respective wall portions of said first and second containers so that said conducting may be moved relative to said occluding cylinder portions to block openings selectively in the wall portions of said conducting means.

7. The combination inhalation and exhalation respiratory therapy device of claim 3 wherein said openings are located in a wall portion of said conducting means exterior of said first and second closed containers and said occluding means comprises a cylindriccal tube portion slideably fitted over said conducting means.

8. The combination inhalation and exhalation respiratory therapy device of claim 1 wherein said conducting means projects through top wall portions of said respective first and second containers.

9. The combination inhalation and exhalation respiratory therapy device of claim 1 wherein said conducting means projects through side wall portions of said first and second containers.

10. A combination inhalation and exhalation respiratory therapy device for use with liquid comprising:
    first and second closed containers;
    means connecting said first and second containers for conducting liquid between said containers having a first open end projecting into said first container to a position adjacent the bottom of said first container and a second open end projecting into said second container to a position adjacent the bottom of said second container;
    means for communicating atmospheric pressure to the surface of the liquid adapted to be contained in said first container projecting through an upper wall portion of said first container;
    tube means communicating through a wall portion of said second container having a first end internal of said second container and adapted to be above the surface of the liquid and having a user end external of said second container into which a person through his mouth may exhale and inhale;
    at least one of said containers or said tube means having at least one opening in a side wall portion thereof for increasing the ratio of the volume of air inhaled from or exhaled into said second container to the volume of the liquid transferred between said containers upon inhalation or exhalation effort respectively applied to said user end of said tube means.

11. An inhalation respiratory therapy device for use with liquid comprising:
    first and second closed containers:
    means projecting through respective wall portions of said containers for conducting liquid between said containers having a first open end located at substantially the bottom of said first container and a second open end located at substantially the bottom of said second container;
    said first container having at least one opening in an upper wall portion thereof for communicating atmospheric pressure to the interior of said first container;

tube means projecting through an upper wall portion of said second container having a user end external of said second container such that a user can apply inhalation effort thereto;

said tube means including one-way valve means for permitting only withdrawal of air from said second container by inhalation effort of said user to said user end of said tube means; and at least one of said containers or said tube means further having at least one opening in a side wall portion thereof for increasing the volume of air withdrawn from said tube means as related to the volume of liquid transferred from said first container to said second container for a given inhalation effort by said user.

12. A combination inhalation and exhalation respiratory therapy device for use with liquid comprising:

first and second closed containers for holding liquid;

means connecting said first and second containers for conducting liquid between said containers, said means having openings in at least two wall portions thereof, said wall portions of said conducting means being located respectively within said first and second containers;

said first container having at least one opening in an upper wall portion thereof communicating atmospheric pressure to the surface of the liquid adapted to be contained therein;

tube means passing through a wall portion of said second container and having a user end external of said second container into which a person may exhale or inhale; and said means for conducting liquid having a first open end next adjacent said opening in the upper wall portion of said first container and having a second open end next adjacent the opening to said tube means in said second container.

13. a combination inhalation and exhalation respiratory therapy device for use with liquid comprising:

first and second closed containers for holding liquid;

means connecting said first and second containers for conducting liquid between said containers, said means for conducting liquid having first and second open ends projecting into said first and second containers respectively to substantially the bottoms thereof;

said first container having at least one opening in an upper wall portion thereof for communicating atmospheric pressure to the interior of said first container;

tube means communicating with the interior of said second container through an upper wall portion and having a user end external of said second container for application of respiratory effort thereto; said tube means having a plurality of openings in a side wall portion thereof; and occluding means mounted on said tube means for selectively occluding openings thereby determining the ratio of air inhaled or exhaled to liquid transferred from said first container to said second container.

* * * * *

UNITED STATES PATENT OFFICE
CERTIFICATE OF CORRECTION

Patent No. 3,977,395    Dated August 31, 1976

Inventor(s) Peter Nelson Brawn

It is certified that error appears in the above-identified patent and that said Letters Patent are hereby corrected as shown below:

Claim 6, column 12, line 13, after ing insert --means--

Signed and Sealed this

Second Day of November 1976

[SEAL]

Attest:

RUTH C. MASON
Attesting Officer

C. MARSHALL DANN
Commissioner of Patents and Trademarks